(12) United States Patent
Wang et al.

(10) Patent No.: US 11,850,081 B2
(45) Date of Patent: *Dec. 26, 2023

(54) MONOCHROMATIC CT IMAGE RECONSTRUCTION FROM CURRENT-INTEGRATING DATA VIA MACHINE LEARNING

(71) Applicant: RENSSELAER POLYTECHNIC INSTITUTE, Troy, NY (US)

(72) Inventors: Ge Wang, Loudonville, NY (US); Wenxiang Cong, Albany, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 123 days.

This patent is subject to a terminal disclaimer.

(21) Appl. No.: 17/460,470

(22) Filed: Aug. 30, 2021

(65) Prior Publication Data

US 2022/0051455 A1    Feb. 17, 2022

Related U.S. Application Data

(63) Continuation of application No. 16/647,220, filed as application No. PCT/US2018/052830 on Sep. 26, 2018, now Pat. No. 11,127,175.

(Continued)

(51) Int. Cl.
*G06T 11/00* (2006.01)
*A61B 6/03* (2006.01)
(Continued)

(52) U.S. Cl.
CPC ............... *A61B 6/032* (2013.01); *G06N 3/04* (2013.01); *G06T 11/006* (2013.01); *G06V 10/60* (2022.01);
(Continued)

(58) Field of Classification Search
CPC ........... G06V 20/176; G06T 7/50; G06T 7/70; G06T 2207/20081; G06T 2207/30184; G06T 2207/20084; G06T 7/73
See application file for complete search history.

(56) References Cited

U.S. PATENT DOCUMENTS

| 7,231,072 B2* | 6/2007 | Yamano | .................. G06T 5/004 |
| | | | 382/128 |
| 2003/0161520 A1* | 8/2003 | Yamano | .................. G06T 5/004 |
| | | | 382/128 |

(Continued)

OTHER PUBLICATIONS

International Search Report and the Written Opinion of the International Searching Authority, International Application No. PCT/US2018/052830, dated Nov. 30, 2018.

*Primary Examiner* — Ping Y Hsieh
(74) *Attorney, Agent, or Firm* — Murtha Cullina LLP; Anthony P. Gangemi

(57) ABSTRACT

A machine-learning-based monochromatic CT image reconstruction method is described for quantitative CT imaging. The neural network is configured to learn a nonlinear mapping function from a training data set to map a CT image, which is reconstructed from a single spectral current-integrating projection data set, to monochromatic projections at a pre-specified energy level, realizing monochromatic CT imaging and overcoming beam hardening.

An apparatus, method and/or system are configured to determine, by a trained artificial neural network (ANN), a monochromatic projection data set based, at least in part, on a measured CT image. The measured CT image may be reconstructed based, at least in part, on measured projection data. The measured projection data may be polychromatic. The apparatus, method and/or system may be further configured to reconstruct a monochromatic CT image based, at least in part, on the monochromatic projection data set.

20 Claims, 5 Drawing Sheets

Related U.S. Application Data

(60) Provisional application No. 62/736,090, filed on Sep. 25, 2018, provisional application No. 62/563,207, filed on Sep. 26, 2017.

(51) Int. Cl.
  *G06N 3/04*    (2023.01)
  *G06V 10/764*  (2022.01)
  *G06V 10/774*  (2022.01)
  *G06V 10/60*   (2022.01)

(52) U.S. Cl.
  CPC .......... *G06V 10/764* (2022.01); *G06V 10/774* (2022.01); *G06T 2207/10081* (2013.01); *G06T 2207/20081* (2013.01); *G06T 2207/20084* (2013.01)

(56) References Cited

U.S. PATENT DOCUMENTS

| | | | |
|---|---|---|---|
| 2012/0213331 A1* | 8/2012 | Peschmann | G01V 5/0016 378/57 |
| 2013/0308745 A1* | 11/2013 | Goshen | A61B 6/52 378/5 |
| 2014/0270440 A1* | 9/2014 | Inglese | A61B 6/4241 382/131 |
| 2018/0197317 A1* | 7/2018 | Cheng | G06T 11/006 |

\* cited by examiner

MONOCHROMATIC CT IMAGE RECONSTRUCTION FROM CURRENT-INTEGRATING DATA VIA MACHINE LEARNING

CROSS REFERENCE TO RELATED APPLICATION(S)

This application is a continuation of and claims the benefit of U.S. Nonprovisional patent application Ser. No. 16/647,220, filed Mar. 13, 2020, that is a national stage application of and claims the benefit of International patent application PCT/US2018/052830, filed Sep. 26, 2018, that claims the benefit of U.S. Provisional Application No. 62/563,207, filed Sep. 26, 2017, and U.S. Provisional Application No. 62/736,090, filed Sep. 25, 2018, the entire disclosures of which are hereby incorporated by reference as if disclosed herein in their entireties.

GOVERNMENT LICENSE RIGHTS

This invention was made with government support under award numbers EB016977 and EB017140, awarded by the National Institutes of Health. The government has certain rights in the invention.

FIELD

The present disclosure related to CT image reconstruction, in particular to, monochromatic CT image reconstruction from current-integrating data via deep learning.

BACKGROUND

Computed tomography (CT) allows visualization and quantification of anatomical and pathological structures with fine spatial/contrast resolution and cost-effectiveness for screening, diagnosis, and therapeutic planning. In clinical CT, the energy spectrum of an x-ray source is polychromatic, and x-ray signals are detected in the current-integrating mode. This physical process is accurately described by an energy-dependent non-linear integral model on the basis of the Beer-Lambert law. The non-linear imaging model is not invertible with an exact analytic solution, and is often approximated as a linear integral model in the form of the Radon transform, basically discarding x-ray energy-dependent information. This model mismatch may generate inaccurate quantification of attenuation image. Because lower energy photons are more easily attenuated than higher energy photons, x-rays spectra may be different at a specific location for different passing ray paths inside the object. Thus the attenuation may be different at the specific location for distinct passing paths, resulting in nonlinear characteristics of the x-rays attenuation. Therefore, the attenuation coefficient reconstructed from the linear integral model in clinical CT may deviate from the true physical quantity of x-ray attenuation, inducing significant beam-hardening artifacts in the image reconstruction.

A linearization technique based on a single material (water for medical CT) correction may transform the measured polychromatic projection data into corresponding monochromatic data via a polynomial correction model. Since water correction ignores the presence of high-density materials, such as bone, it fails to correct the cupping and streak artifacts caused by multiple high-density materials inside the scanned field of view. Single material correction may be extended to the case of multiple material objects using an iterative post reconstruction (IPR) approach. From a preliminary reconstruction, the IPR techniques are configured to estimate the intersection length of each material along every x-ray ray path using image segmentation techniques. Then, a sinogram can be better corrected from material thicknesses and prior knowledge about materials composition and corresponding x-ray spectral information based on the polychromatic x-ray physical model. These single material techniques illustrate feasibility of the x-ray monochromatic imaging using an ordinary x-ray CT scanner. However, the IPR techniques involve a relatively complicated image segmentation procedure, and information of tissue structure and composition, which are not available in medical imaging cases. The beam hardening correction is relatively sensitive to the segmentation accuracy.

SUMMARY

In some embodiments, a method for reconstructing a monochromatic computed tomography (CT) image includes determining, by a trained artificial neural network (ANN), a monochromatic projection data set based, at least in part, on a measured CT image. The measured CT image is reconstructed based, at least in part, on measured projection data. The measured projection data is polychromatic. The method further includes reconstructing, by reconstruction circuitry, the monochromatic CT image based, at least in part, on the monochromatic projection data set.

In some embodiments, the method may further include reconstructing, by CT image reconstruction circuitry, the measured CT image. In some embodiments, the method may further include training, by training circuitry, the ANN based, at least in part, on a dual energy training set. In some embodiments, the method may further include training, by training circuitry, the ANN with a training data set, the training data set including at least one of simulation data and experimental data. In some embodiments, the method may further include training, by training circuitry, the ANN based, at least in part, on a first number of training CT images having a second number of associated projection lines, wherein the second number of associated projection lines is greater than the first number of training CT images, each projection line including a plurality of pixels and the ANN is trained using fewer than all of the pixels.

In some embodiments of the method, the ANN is a multilayer perceptron neural network. In some embodiments of the method, the ANN comprises an input layer, an output layer and at least one hidden layer. In some embodiments of the method, the ANN comprises an input layer, an output layer and three hidden layers.

In some embodiments, the monochromatic CT image may be reconstructed using a reconstruction technique selected from the group comprising filtered back projection (FBP), an iterative technique and/or a dictionary learning based technique. In some embodiments, the monochromatic projection data set may be configured to reduce beam hardening artifacts in the monochromatic CT image compared to the measured CT image.

In some embodiments, a computer readable storage device has stored thereon instructions that when executed by one or more processors result in the following operations including determining, by a trained artificial neural network (ANN), a monochromatic projection data set based, at least in part, on a measured CT image. The measured CT image is reconstructed based, at least in part, on measured projection data. The measured projection data is polychromatic.

The operations further include reconstructing the monochromatic CT image based, at least in part, on the monochromatic projection data set.

In some embodiments, the instructions that when executed by one or more processors may result in the following additional operations including reconstructing the measured CT image. In some embodiments, the instructions that when executed by one or more processors may result in the following additional operations including training the ANN based, at least in part, on a dual energy training data set. In some embodiments, the instructions that when executed by one or more processors may result in the following additional operations including training the ANN with a training data set, the training data set comprising at least one of simulation data and experimental data. In some embodiments, the instructions that when executed by one or more processors may result in the following additional operations including training the ANN based, at least in part, on a first number of training CT images having a second number of associated projection lines, wherein the second number of associated projection lines is greater than the first number of training CT images, each projection line comprises a plurality of pixels and the ANN is trained using fewer than all of the pixels.

In some embodiments of the computer readable storage device, the ANN is a multilayer perceptron neural network. In some embodiments of the computer readable storage device, the ANN includes an input layer, an output layer and at least one hidden layer. In some embodiments of the computer readable storage device, the ANN includes an input layer, an output layer and three hidden layers.

In some embodiments of the computer readable storage device, the monochromatic CT image is reconstructed using a reconstruction technique selected from the group comprising filtered back projection (FBP), an iterative technique and/or a dictionary learning based technique. In some embodiments of the computer readable storage device, the monochromatic projection data set is configured to reduce beam hardening artifacts in the monochromatic CT image compared to the measured CT image.

In some embodiments, an apparatus for reconstructing a computed tomography (CT) image includes a trained artificial neural network (ANN) configured to determine a monochromatic projection data set based, at least in part, on a measured CT image. The measured CT image is reconstructed based, at least in part, on measured projection data. The measured projection data is polychromatic. The apparatus further includes reconstruction circuitry configured to reconstruct the monochromatic CT image based, at least in part, on the monochromatic projection data set.

In some embodiments, the apparatus further includes CT image reconstruction circuitry configured to reconstruct the measured CT image. In some embodiments, the apparatus further includes training circuitry configured to train the ANN based, at least in part, on a dual energy training data set. In some embodiments, the apparatus further includes training circuitry configured to train the ANN with a training data set, the training data set comprising at least one of simulation data and experimental data. In some embodiments, the apparatus further includes training circuitry configured to train the ANN based, at least in part, on a first number of training CT images having a second number of associated projection lines, wherein the second number of associated projection lines is greater than the first number of training CT images, each projection line includes a plurality of pixels and the ANN is trained using fewer than all of the pixels.

In some embodiments of the apparatus, the ANN is a multilayer perceptron neural network. In some embodiments of the apparatus, the ANN includes an input layer, an output layer and at least one hidden layer. In some embodiments of the apparatus, the ANN includes an input layer, an output layer and three hidden layers.

In some embodiments, the monochromatic CT image is reconstructed using a reconstruction technique selected from the group comprising filtered back projection (FBP), an iterative technique and/or a dictionary learning based technique. In some embodiments, the monochromatic projection data set is configured to reduce beam hardening artifacts in the monochromatic CT image compared to the measured CT image.

In some embodiments, a computed tomography (CT) scanner includes an x-ray source; a detector array; and correction circuitry. The correction circuitry includes a trained artificial neural network (ANN) configured to determine a monochromatic projection data set based, at least in part, on a measured CT image. The measured CT image is reconstructed based, at least in part, on measured projection data. The measured projection data is polychromatic. The CT scanner further includes reconstruction circuitry configured to reconstruct the monochromatic CT image based, at least in part, on the monochromatic projection data set.

In some embodiments, the CT scanner further includes CT image reconstruction circuitry configured to reconstruct the measured CT image. In some embodiments of the CT scanner, the correction circuitry further includes training circuitry configured to train the ANN based, at least in part, on a dual energy training data set. In some embodiments of the CT scanner, the correction circuitry further includes training circuitry configured to train the ANN with a training data set. The training data set includes at least one of simulation data and experimental data. In some embodiments of the CT scanner, the correction circuitry further includes training circuitry configured to train the ANN based, at least in part, on a first number of training CT images having a second number of associated projection lines, wherein the second number of associated projection lines is greater than the first number of training CT images. Each projection line includes a plurality of pixels and the ANN is trained using fewer than all of the pixels.

In some embodiments of the CT scanner, the ANN is a multilayer perceptron neural network. In some embodiments of the CT scanner, the ANN comprises an input layer, an output layer and at least one hidden layer. In some embodiments of the CT scanner, the ANN comprises an input layer, an output layer and the hidden layers.

In some embodiments of the CT scanner, the monochromatic CT image is reconstructed using a reconstruction technique selected from the group comprising filtered back projection (FBP), an iterative technique and/or a dictionary learning based technique. In some embodiments of the CT scanner, the monochromatic projection data set is configured to reduce beam hardening artifacts in the monochromatic CT image compared to the measured CT image.

In some embodiments, a computed tomography (CT) image reconstruction system includes at least one device arranged to perform any one of the embodiments of the method.

In some embodiments, a computed tomography (CT) image reconstruction device includes means to perform any one of the embodiments of the method.

In some embodiments, a computer readable storage device having stored thereon instructions that when executed by one or more processors result in the following operations including any one of the embodiments of the method.

BRIEF DESCRIPTION OF THE DRAWINGS

The drawings show embodiments of the disclosed subject matter for the purpose of illustrating features and advantages of the disclosed subject matter. However, it should be understood that the present application is not limited to the precise arrangements and instrumentalities shown in the drawings, wherein.

DETAILED DESCRIPTION

Figure 1:
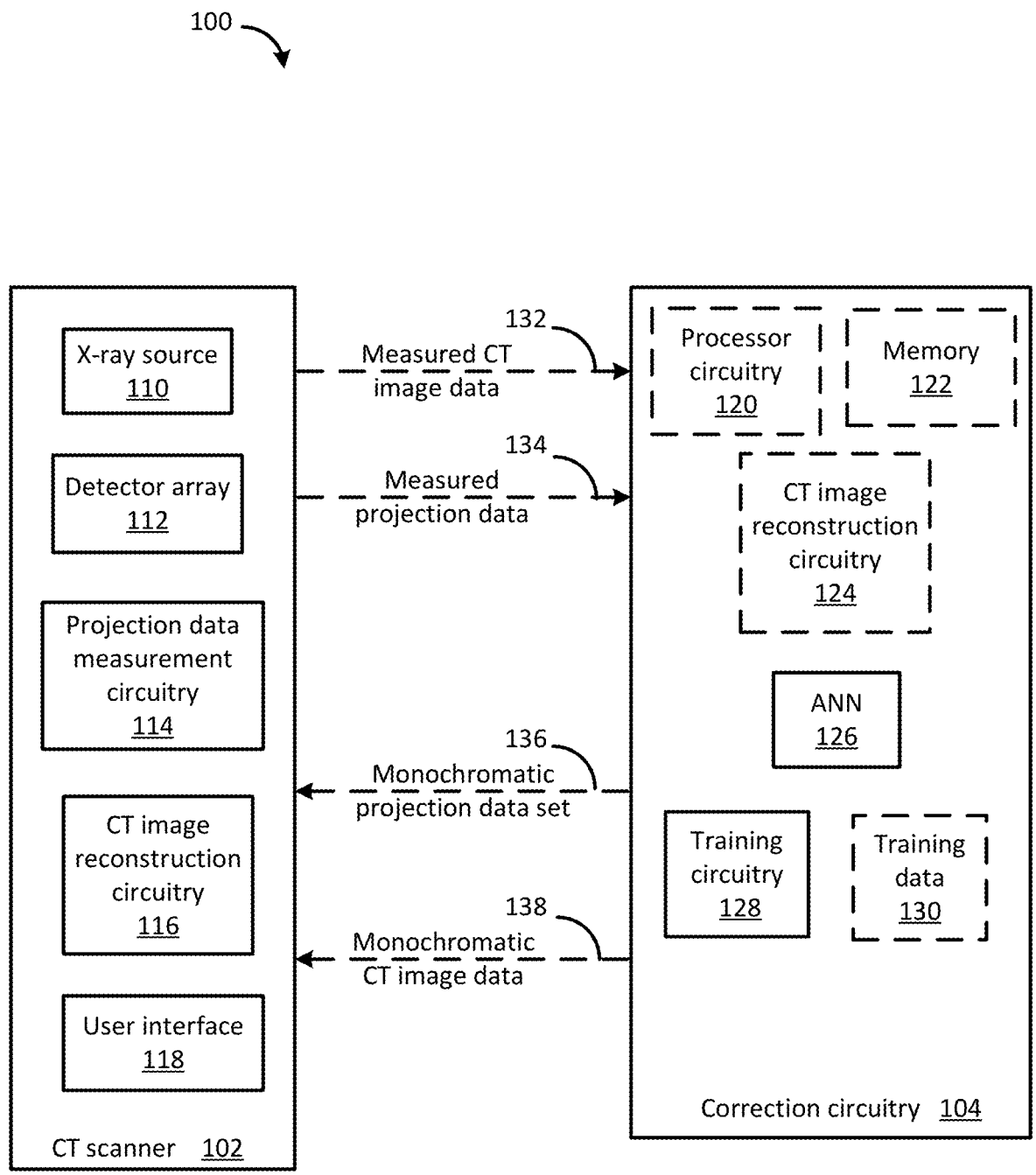
FIG. 1 illustrates a functional block diagram of a computed tomography (CT) image system consistent with several embodiments of the present disclosure.

An artificial neural network (ANN) is a network of elements (e.g., nodes) configured to receive input, change their internal state (activation) according to that input, and produce output depending on the input and activation. The network is formed by connecting the output of selected nodes to the input of other nodes to form a directed, weighted graph. The weights as well as the functions that compute the activation can be modified by learning (e.g., training).

A deep neural network is an ANN that has a plurality of layers between the input and output layers. A relationship between the input and the output may be linear or non-linear. A convolutional neural network (CNN) is a type of deep, feed-forward ANN, that includes one or more convolutional layers with fully connected layers on top. A multilayer perceptron (MLP) is a type of feed-forward ANN that includes at least three layers of nodes and each node, except for the input nodes, uses a nonlinear activation function. An MLP may be trained using back propagation, a supervised learning technique. The multiple layers and non-linear activation of an MLP distinguish it from a linear perceptron. CNNs are a type of deep ANN that use a variation of multilayer perceptrons designed to use minimal preprocessing.

As used herein, the terms "neural network" and "artificial neural network" (ANN) correspond to an artificial neural network, a deep neural network, a convolutional neural network and/or a multilayer perceptron.

Deep learning is a type of machine learning technique that uses a cascade of a plurality of layers of nonlinear processing units for feature extraction and transformation. Each successive layer uses the output from the previous layer as input. Deep learning techniques learn in supervised (e.g., classification) and/or unsupervised (e.g., pattern analysis) manners. Deep learning algorithms learn multiple levels of representations that correspond to different levels of abstraction. In other words, deep-learning methods are representation-learning methods with multiple levels of representation, obtained by composing simple but non-linear modules that each transform the representation at one level into a representation at a higher, slightly more abstract level. With the composition of enough such transformations, very complex functions can be learned.

Deep learning may be utilized in image analysis including, for example, image classification, identification and segmentation. For example, convolutional neural network (CNN) techniques may be utilized for image denoising in low-dose CT. The deep learning CT denoising methods may be configured to learn a function between a low-dose image patch and the corresponding patch of high quality from a large training data set. After this training process, CNN is used to transform a low-dose CT image to a relatively higher quality counterpart. In another example, deep learning for image reconstruction may be utilized to enhance image quality. The deep learning method may be configured to learn a regularization transformation and parameters from big data for iterative reconstruction, complying with natural structures of medical images. In another example, a deep residual network may be configured to suppress artifacts for limited-angle CT image reconstruction.

Generally, the present disclosure relates to a machine learning-based image reconstruction method configured to reduce or eliminate beam-hardening artifacts in a reconstructed CT image. A neural network is configured to learn a nonlinear transform from a training data set to map CT images reconstructed from a single current-integrating data set to monochromatic projections at a pre-specified energy level, realizing monochromatic imaging and overcoming beam hardening effectively on a common clinic CT scanner without any dual-energy function. Machine learning has been successful in image classification, identification, segmentation, and super resolution. For example, convolutional neural network (CNN) techniques may be applied for image denoising in low-dose CT. To train the neural network, the training data can be obtained from a state of the art dual-energy CT scanner, such as Revolution CT with source kVp-switching (available from General Electric Company (GE)), IQon Spectral CT with double-layer detection (available from Philips, N.V.), and Somatom Force CT with dual-source gantry (available from Siemens, A.G.), that may be available in clinical practice to generate dual-energy data sets. In the diagnostic energy range, the x-ray energy-dependent attenuation process can be approximated as a combination of photoelectric absorption and Compton scattering. A dual-energy CT scan generates two projection data sets with two distinct x-ray energy spectra, which can be used to reconstruct photoelectric absorption and Compton scattering components for synthesis of monochromatic projection data sets. To ensure accuracy, uniqueness and stability of the neural network model, the training data set should have a sufficiently high quality and quantity of images with well-diversified features.

One nonlimiting example application of x-ray monochromatic imaging is for proton therapy treatment planning. To improve the prognosis of a patient, proton therapy may be configured to deliver a highly-focused radiation dose to a tumor at the Bragg peak whose position is determined by stopping power ratio (SPR) relative to water along the beam path. A treatment planning activity may include operating an ordinary CT scanner with a single-spectrum current-integrating data set using a stoichiometric calibration method to establish a one-to-one relationship between CT numbers and SPRs for biological tissue. The calibration method may be susceptible to variations of tissue composition. Inaccurate CT numbers induced from beam-hardening artifacts may compromise the radiation dose distribution over a cancerous region. With machine learning-based monochromatic imaging, as described herein, the electron density and effective atomic number of matter composition can be extracted for accurate computation of SPR. Thus, the proton therapy treatment planning can be implemented on an ordinary CT scanner for superior diagnostic and therapeutic performance, reducing system complexity, radiation dose, and planning cost compared with the use of dual-energy CT.

Generally, this disclosure relates to monochromatic CT image reconstruction from current-integrating data via machine learning. An apparatus, method and/or system are configured to determine, by a trained artificial neural network (ANN), a monochromatic projection data set based, at least in part, on a measured CT image. The measured CT image may be reconstructed based, at least in part, on measured projection data. The measured projection data may be polychromatic. The apparatus, method and/or system may be further configured to reconstruct a monochromatic CT image based, at least in part, on the monochromatic projection data set. The monochromatic projection data set is configured to reduce beam hardening artifacts in the monochromatic CT image compared to the measured CT image Thus, a deep-learning-based image reconstruction technique may be utilized for monochromatic CT imaging when an x-ray source is polychromatic, and an x-ray detector is in the current-integrating mode. A nonlinear map (e.g., trained multilayer perceptron) may be determined between directly measured data and idealized line integrals (i.e., monochromatic projection data) through data-driven optimization. Due to big data based learning, the nonlinear mapping is configured to avoid the beam-hardening mechanism. Thus, the inverse Radon transform, such as filtered back projection (FBP), can be applied for monochromatic image reconstruction with relatively high accuracy. A system, method and/or apparatus, consistent with the present disclosure may be utilized for biomedical imaging, nondestructive testing, security screening, and/or other applications.

FIG. 1 illustrates a functional block diagram of a computed tomography (CT) image system 100 consistent with several embodiments of the present disclosure. CT image system 100 includes CT scanner 102 and correction circuitry 104. In an embodiment, correction circuitry 104 may be coupled to CT scanner 102. In another embodiment, correction circuitry 104 may be included in CT scanner 102. CT scanner 102 is configured to generate CT images of an object from detected attenuated x-ray beams. Correction circuitry 104 is configured to determine a monochromatic projection data set based, at least in part, on measured projection data using a trained artificial neural network.

CT scanner 102 includes an x-ray source 110, a detector array 112, projection data measurement circuitry 114, CT image reconstruction circuitry 116 and a user interface 118. User interface 118 may include a user input device (e.g., keyboard, keypad, mouse, touchpad, etc.) and/or a user output device (e.g., a display).

X-ray source 110 is configured to provide a beam of x-rays. The x-ray beams may be polychromatic, i.e., may include more than one energy level. Detector array 112 includes a plurality of detectors configured to detect possibly attenuated x-ray beams from the x-ray source 110. The x-ray beams may pass through, and/or be scattered by, object(s) positioned between the x-ray source 110 and the detector array 112. An amount of attenuation is related to, among other things, characteristics of the object(s). The detector array 112 may be operated in current integrating mode, thus, an output from each detector may include contributions from one or more paths corresponding to one or more energy levels.

Projection data measurement circuitry 114 is configured to receive output from detector array 112 and to determine measured projection data based, at least in part, on the output from the detector array 112. The measured projection data may be displayed, for example, on the user interface 118, as a sinogram. CT image reconstruction circuitry 116 is configured to receive projection data (measured and/or monochromatic) and to reconstruct a corresponding CT image based, at least in part, on the received projection data. As used herein, "measured projection data" corresponds to projection data that is polychromatic and "monochromatic projection data" corresponds to projection data that is monochromatic, as will be described in more detail below.

Correction circuitry 104 may include, but is not limited to, a microcomputer, a microcontroller, a computing device, a field programmable gate array (FPGA), an application-specific integrated circuit (ASIC), a complex programmable logic device (CPLD), a programmable logic device (PLD), etc. Correction circuitry 104 may include processor circuitry 120, memory 122 and/or CT image reconstruction circuitry 124. Correction circuitry 104 includes artificial neural network (ANN) 126 and training circuitry 128. In an embodiment, correction circuitry 104 includes CT image reconstruction circuitry 124. In another embodiment, correction circuitry 104 may not include CT image reconstruction circuitry 124 and, in this embodiment, CT image reconstruction operations may be performed by CT image reconstruction circuitry 116 included in CT scanner 102.

Processor circuitry 120 may include, but is not limited to, a single core processing unit, a multicore processor, a graphics processing unit, a microcontroller, an application-specific integrated circuit (ASIC), a field programmable gate array (FPGA), a programmable logic device (PLD), etc. Processor circuitry 120 may be configured to perform one or more operations of CT image reconstruction circuitry 124, ANN 126 and/or training circuitry 128. Memory 122 may be configured to store information and/or data associated with CT image reconstruction circuitry 124, ANN 126 and/or training circuitry 128.

Training circuitry 128 is configured to acquire training data 130 and to manage training ANN 126, as described herein. In one example, training circuitry 128 may be configured to generate a training data set from simulation data and/or experimental data. Simulation techniques may include, but are not limited to, x-ray Monte Carlo simulation and/or a computer-assisted tomography simulation environment. In another example, training circuitry 128 may be configured to generate a training data set, e.g., a dual energy training data set, using dual energy CT techniques.

Training data 130 may include one or more training data sets. In one example, a training data set may correspond to a dual energy training data set. In another example, a training data set may not correspond to a dual energy data set. Each training data set may include a training monochromatic projection data set, training CT image data corresponding to a training CT image and/or training measured projection data. The training CT image data and/or training measured projection data are configured to be polychromatic. The training monochromatic projection data set is configured to be monochromatic. The training CT image data may then correspond to input data and the training monochromatic projection data set may then correspond to output data for training an artificial neural network, e.g., ANN 126. Thus, training data 130 may be used to train ANN 126, as will be described in more detail below.

In an embodiment, correction circuitry 104 may be configured to receive measured CT image data 132 corresponding to a measured CT image from CT scanner 102. In this embodiment, CT image reconstruction circuitry 116 may be configured to reconstruct the measured CT image based, at least in part, on measured projection data 134 received from projection data measurement circuitry 114. In another embodiment, correction circuitry 104 may be configured to receive measured projection data 134 from CT scanner 102. In this embodiment, measured projection data 134 may be determined by projection data measurement circuitry 114 based, at least in part, on output from detector array 112. CT image reconstruction circuitry 124 may then be configured to reconstruct the measured CT image based, at least in part, on the measured projection data 134.

In an embodiment, correction circuitry 104 is configured to provide a monochromatic projection data set 136 to CT scanner 102. The CT image reconstruction circuitry 116 may then be configured to reconstruct a monochromatic CT image based, at least in part, on the monochromatic projection data set 136. The monochromatic projection data set 136 may be determined by ANN 126 based, at least in part, on a measured CT image and corresponding measured CT image data. The measured CT image data provided to ANN 126 may correspond to measured CT image data 132 and/or may correspond to a measured CT image reconstructed based, at least in part, on measured projection data 134.

In another embodiment, correction circuitry 104 is configured to provide monochromatic CT image data 138 corresponding to a monochromatic CT image to CT scanner 102. The monochromatic CT image data 138 may be provided from CT image reconstruction circuitry 124. In this embodiment, CT image reconstruction circuitry 124 may be configured to reconstruct the monochromatic CT image based, at least in part, on a monochromatic projection data set. The monochromatic projection data set 136 may be determined by ANN 126 based, at least in part, on a measured CT image data.

Thus, ANN 126 may be trained based, at least in part, on training data 130. ANN 126 may then be utilized to determine a monochromatic projection data set based, at least in part, on a measured CT image, the measured CT image reconstructed based, at least in part, on measured projection data. The measured projection data may be polychromatic and the monochromatic projection data set is configured to be monochromatic. A monochromatic CT image may then be reconstructed based, at least in part, on the monochromatic projection data set. The monochromatic CT image may then have fewer (if any) beam hardening artifacts compared to the measured CT image.

In an embodiment consistent with the present disclosure, a deep-learning-based reconstruction technique is configured to reduce and/or eliminate beam-hardening artifacts in a CT image reconstructed from current-integrating data. The technique includes development of a nonlinear transformation in the form of a neural network (e.g., ANN 126) through a training process with big data (e.g., training data 130). This deep learning-based transform is configured to correct measured projection data to accurately match the linear integral model at a target energy level, allowing beam hardening reduction and realizing monochromatic imaging.

In medical CT, the x-ray source (e.g., x-ray source 110) generally emits polychromatic x-ray photons. The x-ray linear attenuation coefficient in the object depends on the material composition of the object and the photon energy. After an x-ray beam passes through the object, the x-ray intensity I(l) may be measured by a current-integrating detector (e.g., included in detector array 112). For example, the x-ray transmitted beam intensity may be described by a non-linear integral model as:

$$I(l) = \int_{E_{min}}^{E_{max}} S(E)D(E) \exp\left(-\int_l \mu(r, E)\, dr\right) dE, \quad (1)$$

where S(E) is the energy spectrum of the x-ray source, D(E) is detection efficiency and u(r, E) is the linear attenuation coefficient at an energy E and a spatial position r along a linear path l through the object.

During propagation through the object, due to interactions between x-rays and the object, the x-ray photons are attenuated according to Equation (Eq.) (1). According to the integral mean value theorem, there is an energy $\varepsilon_l$ for each x-ray path such that:

$$\begin{cases} I(l) = I_0(l) \exp\left(-\int_l \mu(r, \varepsilon_l)\, dr\right) & (2A) \\ I_0(l) = \int_{E_{min}}^{E_{max}} S(E)D(E)\, dE & (2B) \end{cases}$$

Equations (2A) and (2B) are equivalent to:

$$\int_l \mu(r, \varepsilon_l)\, dr = \log\left[\frac{I_0(l)}{I(l)}\right] \quad (3)$$

where $I_0(l)$ is the detected x-ray intensity along path l without an object in the field of view. During a CT scan, x-rays traversing different paths through the object are likely to have different spectra, that is, the different paths correspond to different energy levels $\varepsilon_l$ in Eq. (3). The disagreement in energy levels at different paths may result in beam hardening artifacts in a directly reconstructed CT image (i.e., measured CT image).

A nonlinear relationship, e.g., a function mapping from machine learning, may be determined, configured to transform measured polychromatic projection data $\{\log[I_0(l)/I(l)]\}$ to monochromatic projection data $\{\log[I_0(l,\varepsilon)/I(l,\varepsilon)]\}$ on a given (i.e., specific) energy level $\varepsilon$, which is defined in the detectable energy range. Generally, from the perspective of information theory, it is not feasible to obtain a direct mapping relation from a single polychromatic view log[I_0

(l)/I(l)] to a corresponding monochromatic view (i.e., a monochromatic counterpart) $\log[I_0(l,\varepsilon)/I(l,\varepsilon)]$ due to a lack of relevant information for an inversion. An image $\mu^*(r)$ (i.e., measured CT image) may be reconstructed from measured projection data $\{\log[I_0(l)/I(l)]\}$ collected at many viewing angles. The image may then contain information regarding object structure and x-ray attenuation along the associated x-ray paths.

In other words, while the image $\mu^*(r)$ reconstructed from raw data $\{\log[I_0(l)/I(l)]\}$ contains abundant information in object structure and x-ray attenuation along the associated x-ray paths, a practical method may be to map pixel values along an x-ray path in the image $\mu^*(r)$ to the monochromatic projection data $\{\log[I_0(l,\varepsilon)/I(l,\varepsilon)]\}$ at the specific energy level $\varepsilon$ and to establish a relationship through machine learning. Mathematically, an optimization model in a machine learning framework may be written as:

$$M = \arg\min \sum_{l \in all\,path\,set} \left\| M(\mu^*(r) \mid r \in l) - \log\left[\frac{I_0(l,\varepsilon)}{I(l,\varepsilon)}\right] \right\| \quad (4)$$

where M denotes a multi-layer perceptron (MLP) neural network, $\mu^*(r)$ corresponds to attenuation coefficients reconstructed from a single current-integrating projection data set, $I_0(l,\varepsilon)$ and $I(l,\varepsilon)$ are the monochromatic projection data at a pre-specified energy level $\varepsilon$ without and with an image object in the field of view, respectively, and l is an x-ray path indexed by the location variable r. If M is simply taken as an identity transformation, it would generate the current-integrating (i.e., measurement) projection data $\{\log[I_0(l)/I(l)]\}$. A well-trained MLP neural network corresponds to a nonlinear transform M configured to map the CT image from a clinical single spectral CT scanner to the ideal monochromatic data $\log[I_0(l,\varepsilon)/I(l,\varepsilon)]$ at the energy level $\varepsilon$.

Once the monochromatic projection data set is obtained through machine learning, a monochromatic image $\mu(r,\varepsilon)$ can be reconstructed using a suitable technique, based on a line integral model (e.g., Radon transform):

$$\int_l \mu(r,\varepsilon)\,dr = \log\left[\frac{I_0(l,\varepsilon)}{I(l,\varepsilon)}\right]. \quad (5)$$

Suitable techniques may include, but are not limited to, filtered back projection (FBP), iterative techniques and/or dictionary learning based techniques.

Thus, a monochromatic CT image can be reconstructed from current-integrating projection data utilizing Eqs. (4) and (5), configured to overcome beam-hardening artifacts.

Figures 2A, 2B:
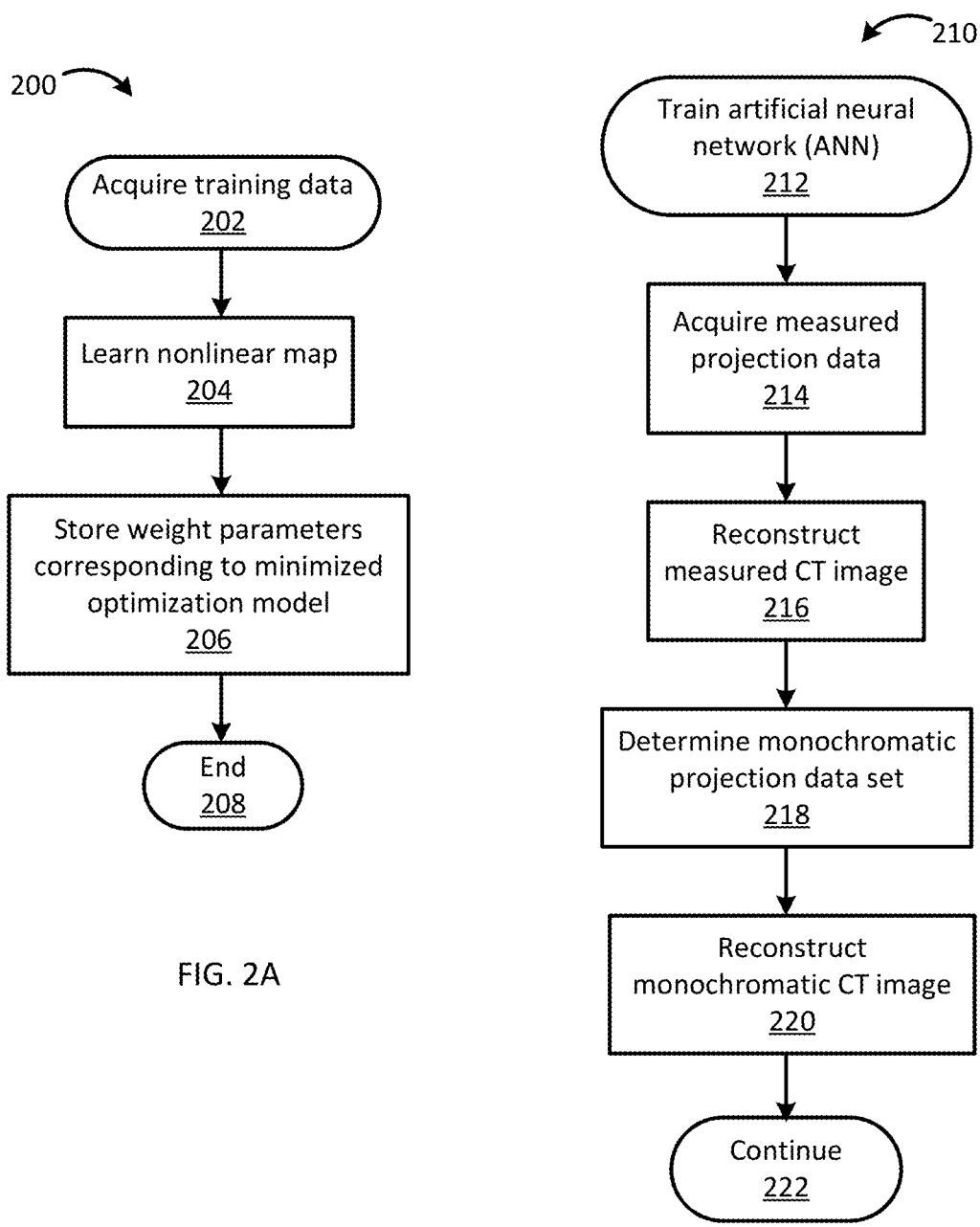
FIG. 2A is a flowchart of example artificial neural network training operations consistent with several embodiments of the present disclosure.
FIG. 2B is an example flowchart of CT image reconstruction operations consistent with several embodiments of the present disclosure.

FIG. 2A is a flowchart 200 of example artificial neural network training operations consistent with several embodiments of the present disclosure. In particular, flowchart 200 illustrates acquiring training data and learning a nonlinear map (i.e., training an ANN) to minimize a cost function (i.e., optimization model). The operations of flowchart 200 may be performed by, for example, correction circuitry 104 (e.g., processor circuitry 120, CT image reconstruction circuitry 124, ANN 126 and/or training circuitry 128) of FIG. 1.

Operations of flowchart 200 may begin with acquiring training data at operation 202. In one example, acquiring training data may include generating a training data set from simulation data and/or experimental data. The simulation data may correspond to a training data set that includes training CT image data and the training projection data sets. In another example, acquiring training data may include generating the training data set using dual energy CT techniques. In this example, the training data set may correspond to a dual energy training data set.

A neural network for tomographic imaging may be trained with a relatively large training data set to optimize its performance. In one nonlimiting example, a training data set may include CT scanning data (e.g., measured projection data and corresponding measured CT image data) of ten objects (e.g., patients) and CT scanning data of three objects (e.g., patients) for testing. The training data set may be generated from simulation data and/or experimental data. Simulation data may be utilized to establish big training data. For example, simulated big training data may be configured to provide a pre-trained network that may then be fine-tuned with experimental data. In one example of simulation data, standard CT images in a Medical Image Library were used to generate x-ray-energy-dependent attenuation images, as described herein.

As is known, photoelectric absorption and Compton scattering are two dominant x-ray attenuation processes over the diagnostic energy range (e.g., 20-140 keV (kilo electron volts)). An x-ray linear attenuation coefficient can be decomposed into a linear combination of photon-electric effect and Compton scattering. Thus, for compound matter composed of k types of basic elements, e.g., biological tissues, the x-ray linear attenuation coefficient can be represented as:

$$\mu(r,\varepsilon) = \sum_{i=1}^{k} w_i \rho_i \frac{N_A}{A_i}(\sigma_{i,ph} + \sigma_{i,co}) \quad (6)$$

where $w_i$ is the proportion by weight of the i-th constituent element, $N_A$ is Avogadro's number ($6.022 \times 10^{23}$ atom/g-atom), $\rho_i$ is the mass density of the i-th element, $A_i$ is atomic weight of the i-th element, $\sigma_{i,ph}$ is the photoelectric atomic cross section for the i-th element, $\sigma_{i,co}$ is the Compton atomic cross section for the i-th element. In term of both photoelectric and Compton atomic cross section, the associated linear attenuation coefficients can be expressed as a product of spatial-dependent and energy-dependent components:

$$\mu(r,\varepsilon) = \sum_{i=1}^{k} w_i(a_i(r)p(\varepsilon) + c_i(r)q(\varepsilon)) \quad (7)$$

where $$a_i(r) = \rho_i Z_i^4 / A_i \quad (7a)$$

is the spatial-dependent photoelectric component for the i-th element, $Z_i$ is the atomic number of the i-th element, $$c_i(r) = \frac{\rho_i Z_i}{A_i} \quad (7b)$$

is the spatial-dependent Compton scattering component for the i-th element, $$p(\varepsilon) = N_A \alpha^4 \frac{8}{3} \pi r_e^2 \sqrt{\frac{32}{\varepsilon^7}} \quad (7c)$$

is the energy-dependent photoelectric component where $\varepsilon=E/511$ keV, $\alpha$ is the fine-structure constant ($\approx 1/137$), and $r_e=2.818$ fm is the classical radius of an electron, and $$q(\varepsilon)=N_A f_{kn}(\varepsilon) \tag{7d}$$

is the energy-dependent Compton scattering component, where $f_{kn}$ is the Klein-Nishina function:

$$f_{kn}(\varepsilon) = 2\pi r_e^2 \left( \frac{1+\varepsilon}{\varepsilon^2} \left[ \frac{2(1+\varepsilon)}{1+2\varepsilon} - \frac{1}{\varepsilon}\ln(1+2\varepsilon) \right] + \frac{1}{2\varepsilon}\ln(1+2\varepsilon) - \frac{1+3\varepsilon}{1+2\varepsilon^2} \right). \tag{7e}$$

Eq. (7) may be rewritten as:

$$\mu(r,\varepsilon)=p(\varepsilon)a(r)+q(\varepsilon)c(r) \tag{8}$$

where $$a(r) = \sum_{i=1}^{k} w_i a_i(r) \tag{8a}$$

$$c(r) = \sum_{i=1}^{k} w_i c_i(r). \tag{8b}$$

Biological tissues are compounds from mostly light elements including hydrogen, carbon, oxygen, nitrogen, fluorine, sodium, magnesium, aluminum, silicon, phosphorus, sulfur, chlorine, argon, potassium, calcium, calcium, iron, and others. Given the tissue types in the CT images, the atomic number (Z), mass density (ρ), and atomic mass (A) may be determined from the database at the National Institute of Standards and Technology (NIST) (https://www.nist.gov) in terms of the attenuation coefficients for every pixel value. Thus, the energy-dependent attenuation coefficients images may be obtained based, at least in part, on Eqs. (6-8).

Simulated current-integrating projection data sets can be generated from the energy-dependent attenuation images. For example, simulation techniques may include, but are not limited to, x-ray Monte Carlo simulation and/or a computer-assisted tomography simulation environment. One example computer-assisted tomography simulation environment "CatSim", developed by GE Global Research Center, incorporates polychromaticity, realistic quantum and electronic noise models, finite focal spot size and shape, finite detector cell size, and detector cross-talk for realistic simulation of the entire x-ray imaging process.

Dual-energy CT may be utilized to generate data sets for training neural networks. Dual-energy CT techniques include source kVp-switching, double-layer detection, dual-source gantry, and two-pass scanning. Dual-energy CT is configured to reconstruct images of an object from two projection data sets generated with two distinct x-ray energy spectra. It can provide more accurate attenuation quantification than conventional CT with a single x-ray energy spectrum. In the diagnostic energy range, x-ray energy-dependent attenuation can be approximated as a combination of photoelectric absorption and Compton scattering. Hence, monochromatic images can be reconstructed in image-domain or projection-domain from dual-energy raw projection data sets, generating spectrally informative projection data sets.

An artificial neural network used for tomographic imaging may be trained with a relatively large data set. The relatively large data set is configured to optimize performance of the trained ANN. The training data set may include conventional (i.e., measured) CT images and their corresponding monochromatic projection data. To facilitate accuracy, uniqueness and stability of the solution, the training data set should have a sufficiently high quantity of images with well-diversified features. In one nonlimiting example, the monochromatic projection data may be obtained from dual energy CT. Examples of dual energy CT scanners include a source kVp-switching CT scanner (available from General Electric Corp. (GE)), a double layer detection CT scanner (available from Philips), a dual source gantry CT scanner (available from Siemens) and two pass scanning CT scanner (available from Toshiba). Dual energy CT is able to reconstruct monochromatic images of an object from two projection data sets generated with two distinct x-ray energy spectra, and provides more accurate attenuation quantification than conventional CT with a single x-ray energy spectrum. Dual energy CT is configured to provide complete energy dependent information under the assumption of two basis materials.

Turning again to FIG. 2A, operation 204 may include learning a nonlinear map (i.e., training an ANN). For example, learning the nonlinear map may include adjusting weight parameters associated with an artificial neural network to minimize a cost function, i.e., an optimization model, as described herein. The nonlinear map may be learned based, at least in part, on one or more training data sets. Each training data set may include a training image set corresponding to measured CT image data and a training projection data set corresponding to a monochromatic projection data set.

In some embodiments, the ANN may be trained based, at least in part, on a dual energy training data set. In some embodiments, the ANN may be trained with a training data set that includes at least one of simulation data and experimental data. In some embodiments, the ANN may be trained based, at least in part, on a first number of training CT images having a second number of associated projection lines, wherein the second number of associated projection lines is greater than the first number of training CT images, each projection line including a plurality of pixels and the ANN is trained using fewer than all of the pixels.

A multi-layer perceptron (MLP) neural network may be configured to perform deep learning based, at least in part, on Eq. (4). In other words, an MLP may be configured to realize an optimization model for x-ray monochromatic imaging based, at least in part, on Eq. (4). The attenuation coefficient $\mu^*(r)$ at location r is an energy spectral weighted average of the energy-dependent attenuation coefficient $\mu(r,\varepsilon)$. X-ray spectra at a specific location may differ due to beam-hardening effect, resulting in an inaccurate quantification of an x-ray linear attenuation coefficient. The trained MLP neural network model M, as described herein, is configured to transform $\mu^*(r)$ to a monochromatic sinogram at a specified energy to correct the beam-hardening.

The MLP neural network may include a plurality of layers. Each layer is configured to contain a plurality of nodes. For example, the MLP neural network may include an input layer, one or more hidden layers, and an output layer. In one nonlimiting example, the MLP neural network may include five layers: an input layer, three hidden layers, and an output layer. In this example, each layer is configured to contain a 1024 nodes. Each node is fully connected to the nodes in a subsequent layer. A sigmoid activation function may be utilized for hidden layers in the neural network. Input to the neural network may include CT image pixel values (i.e., measured CT image data) $\mu^*(r)$ on an x-ray path l. The output is configured to correspond to an x-ray monochromatic projection (i.e., monochromatic projection data) along the same path. The hidden nodes are configured to form weighted combinations of output units on the previous layer and perform corresponding non-linear activations. The output may be a composition function defined as:

$$M(X) = \sum_{s=1}^{N} w_{t,s}^{(n)} \sigma \left[ \ldots \sigma \left( \sum_{j=1}^{N} \left( w_{k,j}^{(2)} \sigma \left( \sum_{i=1}^{N} w_{j,i}^{(1)} x_i + b_i^{(1)} \right) + b_j^{(2)} \right) \right) \right] + b_s^{(n)}, \quad (9)$$

where $\sigma(\cdot)$ is an activation function, and $w_{j,i}^{(n)}$ is the weight for the link between the $j^{th}$ node of the current layer and the $i^{th}$ node of the previous layer, and $b_k^{(n)}$ is the bias at the $k^{th}$ node of the $n^{th}$ layer. The output layer is configured to contain a single node, yielding a weighted linear combination of all the node units on the last hidden layer, i.e., the hidden layer prior to the output layer.

Figure 3:
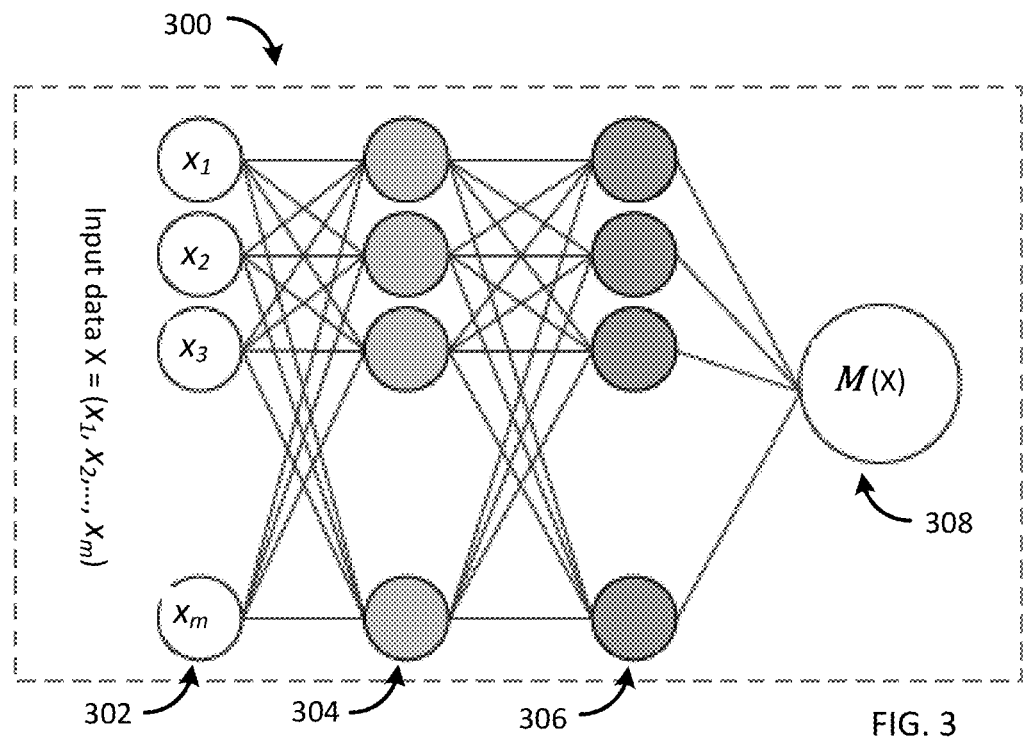
FIG. 3 illustrates an example artificial neural network (ANN) multilayer perceptron (MLP)

FIG. 3 illustrates an example artificial neural network (ANN) multilayer perceptron (MLP) 300. MLP 300 includes an input layer 302, a first hidden layer 304, a second hidden layer 306 and an output layer 308. The input layer 302 is configured to receive an array, X, of input data, e.g., $X=(x_1, x_2, \ldots, x_m)$. The output layer 308 includes one element: M(X).

An MLP may have an optimal number of hidden layers. The optimal number of hidden layers in the MLP is related to the complexity of the function to be learned. For example, too few hidden layers may suffer from training errors due to under fitting. In another example, too many hidden layers may result in over fitting, reducing convergence speed and network performance. The optimal number of hidden layers can be found iteratively using a heuristic technique.

The MLP neural network is a supervised learning technique that learns a function M: $R^m \rightarrow R$ by training on a data set $\{(X,y)|(X_1,y_1), (X_2,y_2), \ldots, (X_N,y_N)\}$, where N is a total number of x-ray paths l though all CT images in the training data set (i.e., training CT images), X is a vector that includes pixel values on x-ray path l in the training CT images, m is the dimension of the input vector X and is defined by the maximum pixel number on attenuation image $\mu^*(r)$ that interacted with x-ray path l and y is a value of x-ray monochromatic projection at the specific energy level along x-ray path l. The variables in the optimization model are weight parameters in the neural network.

Turning again to FIG. 2A, operation 206 may include storing the weight parameters corresponding to the minimized optimization model. For example, storing the weight parameters may correspond to setting weights and/or functions in ANN 126. Program flow may then end at operation 208.

Thus, an artificial neural network may be trained based, at least in part, on training data and based, at least in part, on an optimization model.

Table 1 illustrates one example monochromatic image reconstruction technique. Table 1 corresponds to FIG. 3 and is configured to implement Eq. 4, as described herein.

TABLE 1

| | |
|---|---|
| A. | Input: Raw (i.e., measured) projection data acquired from CT scanner (e.g., CT scanner 102) operating in a current-integrating detection mode; |
| B. | Perform image reconstruction from raw projection data using, for |

TABLE 1-continued

| | |
|---|---|
| | example, FBP; |
| C. | Learn a nonlinear transform on a neural network (e.g., MLP) from a training data set to determine a monochromatic projection data set: |
| | $$M = \text{argmin} \sum_{l \in \text{all path set}} \left\| M(\mu^*(r) \mid r \in l) - \log\left[\frac{I_0(l, \varepsilon)}{I(l, \varepsilon)}\right] \right\|$$ |
| D. | Reconstruct a monochromatic CT image from monochromatic projection data set; |
| E. | Output: Reconstructed monochromatic CT image. |

FIG. 2B is a flowchart 210 of example CT image reconstruction operations consistent with several embodiments of the present disclosure. In particular, the flowchart 210 illustrates determining a monochromatic projection data set using a trained artificial neural network and reconstructing a monochromatic CT image based, at least in part, on the monochromatic projection data set. The operations of flowchart 210 may be performed by, for example, CT scanner 102 (e.g., projection data measurement circuitry 114 and/or CT image reconstruction circuitry 116) and/or correction circuitry 104 (e.g., processor circuitry 120, CT image reconstruction circuitry 124, artificial neural network 126, and/or training circuitry 128) of FIG. 1.

Operations of flowchart 210 may begin with training an artificial neural network (ANN) at operation 212. The ANN may be trained according to operations of flowchart 200 of FIG. 2A and as described herein. After the ANN has been trained, the ANN may be utilized to determine a monochromatic projection data set based, at least in part, on a measured CT image. Measured projection data may be acquired at operation 214. For example, the measured projection data may be acquired from projection data measurements circuitry 114 of FIG. 1. A measured CT image may then be reconstructed at operation 216. In one example, the measured CT image may be reconstructed by CT image reconstruction circuitry 116 included in CT scanner 102. In another example, the measured CT image may be reconstructed by CT image reconstruction circuitry 124 included in correction circuitry 104.

A monochromatic projection data set may then be determined at operation 218. For example, the monochromatic projection data set may be determined by ANN 126. The monochromatic projection data set may be determined based, at least in part, on the measured CT image reconstructed based, at least in part, on the measured projection data. A monochromatic CT image may then be reconstructed at operation 220. In one example, the monochromatic CT image may be reconstructed by CT image reconstruction circuitry 116 included in CT scanner 102. In another example, the monochromatic CT image may be reconstructed by CT image reconstruction circuitry 124 included in correction circuitry 104. Program flow may then continue at operation 222. For example, operations 214, 216, 218 and 220 may be repeated for new measured projection data.

Thus, an ANN may be trained and the ANN may then be utilized to determine a monochromatic projection data set based, at least in part, on a measured CT image, the measured CT image reconstructed based, at least in part, on measured projection data. The measured projection data may be polychromatic and the monochromatic projection data set is configured to be monochromatic. A monochromatic CT image may then be reconstructed based, at least in part, on the monochromatic projection data set. The monochromatic CT image may then have fewer (if any) beam hardening artifacts compared to the measured CT image.

Example

Figure 4:
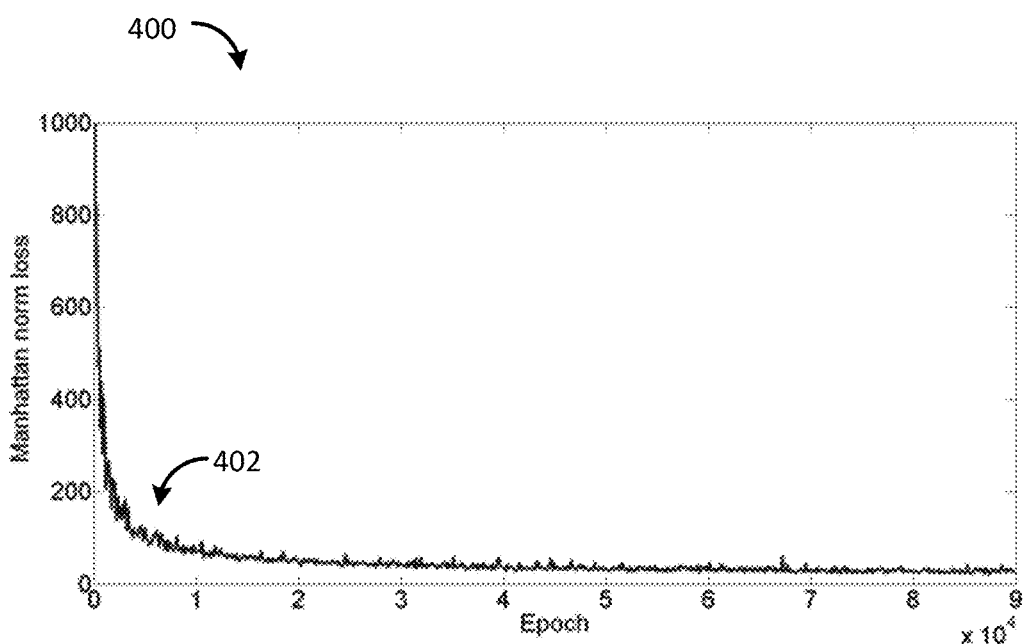
FIG. 4 is a plot illustrating convergence during training for one embodiment consistent with the present disclosure.

FIG. 4 is a plot 400 illustrating convergence during training for one embodiment consistent with the present disclosure. In plot 400, a horizontal axis corresponds to epoch and a vertical axis corresponds to a Manhattan norm loss. Plot 400 includes a convergence curve 402 for an optimization model (corresponding to Eq. 4, in this example) during training.

In this nonlimiting example, a clinical multi-energy CT data set of the human abdomen generated from a GE Discovery CT750 dual-energy scanner at Ruijin Hospital in Shanghai, China, was used for training and testing a MLP neural network, as described herein. A multi-energy data set included 6 energy bins: 50 kev, 50 kev, 70 kev, 80 kev, 90 kev and 100 kev. A training data set included 274 CT images slices in each energy bin reconstructed from raw data (i.e., measured projection data) acquired from two patients. A test data set included 157 CT images slices in each energy bin reconstructed from raw data acquired from another patient. 274 CT images as input data were reconstructed from a single spectral current-integrating projection data set (i.e., measured projection data set) synthesized by the multi-energy data set. A corresponding 274 monochromatic images (i.e., training monochromatic CT images) in the 80 keV energy channel were used as labeled images of training data set for the example MLP neural network. The 274 image pairs generated 122 million x-ray paths for the training data set. The training procedure was programmed in Python on the TensorFlow on a PC computer with a NVIDIA Titan XP GPU and 12 GB memory. The neural network was trained using an Adam optimization algorithm. Data was sampled randomly over the training data set, to facilitate finding the global minimum. As illustrated in FIG. 4, the MLP neural network training, as described herein, showed an excellent converging behavior, and its cost function decreased towards a global minimum.

Figure 5A:
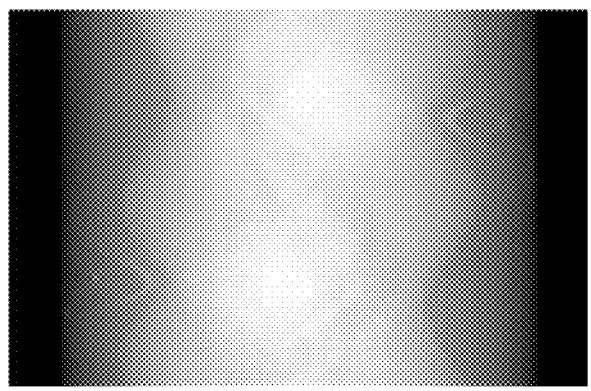
FIGS. 5A and 5B illustrate a ground truth sinogram and a corresponding monochromatic sinogram according to one embodiment of the present disclosure, respectively.
Figure 5B:
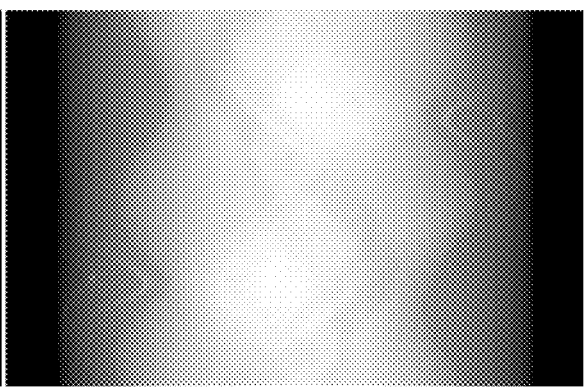

FIGS. 5A and 5B illustrate a ground truth sinogram 500 and a corresponding monochromatic sinogram 502 according to one embodiment of the present disclosure, respectively. FIGS. 5C through 5F are plots of x-ray intensity versus detector index for a first 504, $136^{th}$ 506, $252^{nd}$ 508 and $408^{th}$ 510 projection view, respectively, for the ground truth sinogram 500 of FIG. 5A and the corresponding monochromatic sinogram 502 of FIG. 5B.

To assess the performance of the trained network using the technique listed in Table 1, polychromatic CT images (i.e., measured CT images) were input to a trained neural network to produce monochromatic projection data. In this example, 157 CT images were reconstructed from a single spectral current-integrating projection data set synthesized by the multi-energy data set to assess the performance of the trained neural network. 157 CT images were input to the trained MLP neural network to produce monochromatic projection data. A random selection of CT images in the testing data set were presented as examples to show the quality of the monochromatic imaging.

Figure 5C:
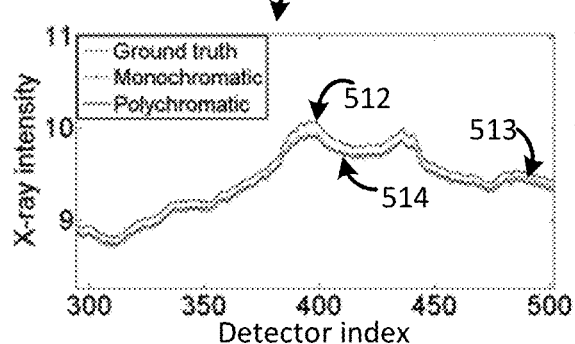
FIGS. 5C through 5F are plots of x-ray intensity versus detector index for a first, $136^{th}$, $252^{nd}$ and $408^{th}$ projection views, respectively, for the ground truth sinogram of FIG. 5A and the corresponding monochromatic sinogram of FIG. 5B.
Figure 5D:
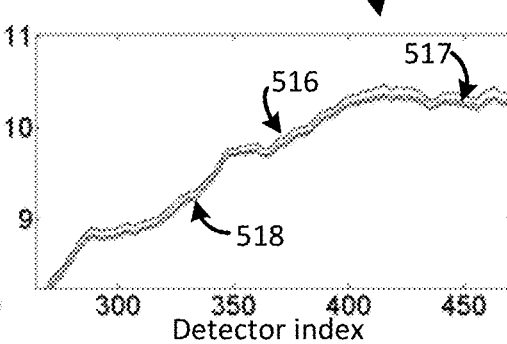
Figure 5E:
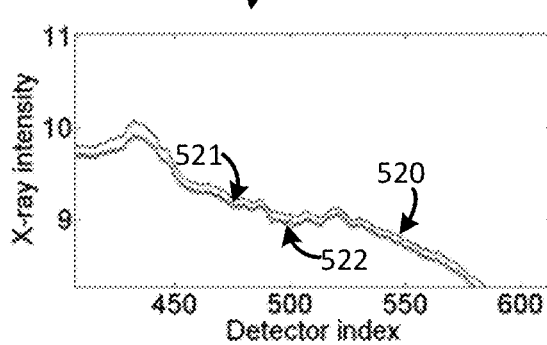
Figure 5F:
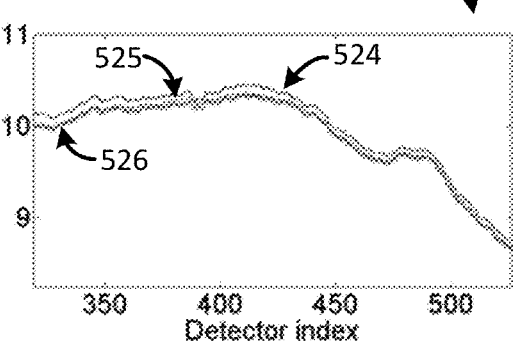

FIGS. 5A and 5B illustrate a comparison of a monochromatic sinogram 502 to a ground truth sinogram 500. FIGS. 5C through 5F illustrate a comparison of x-ray intensity versus detector index for several view projections. For example, FIG. 5C is a plot 504 of x-ray intensity versus detector index for a first projection view and includes a polychromatic projection view 512, a ground truth projection view 513 and a monochromatic projection view 514. Similarly, FIG. 5D is a plot 506 of x-ray intensity versus detector index for a 136th projection view and includes a polychromatic projection view 516, a ground truth projection view 517 and a monochromatic projection view 518; FIG. 5E is a plot 508 of x-ray intensity versus detector index for a 252nd projection view and includes a polychromatic projection view 520, a ground truth projection view 521 and a monochromatic projection view 522; and FIG. 5F is a plot 508 of x-ray intensity versus detector index for a 408th projection view and includes a polychromatic projection view 524, a ground truth projection view 525 and a monochromatic projection view 526. Then, the image reconstruction was performed using FBP from the monochromatic projection data.

Figure 6A:
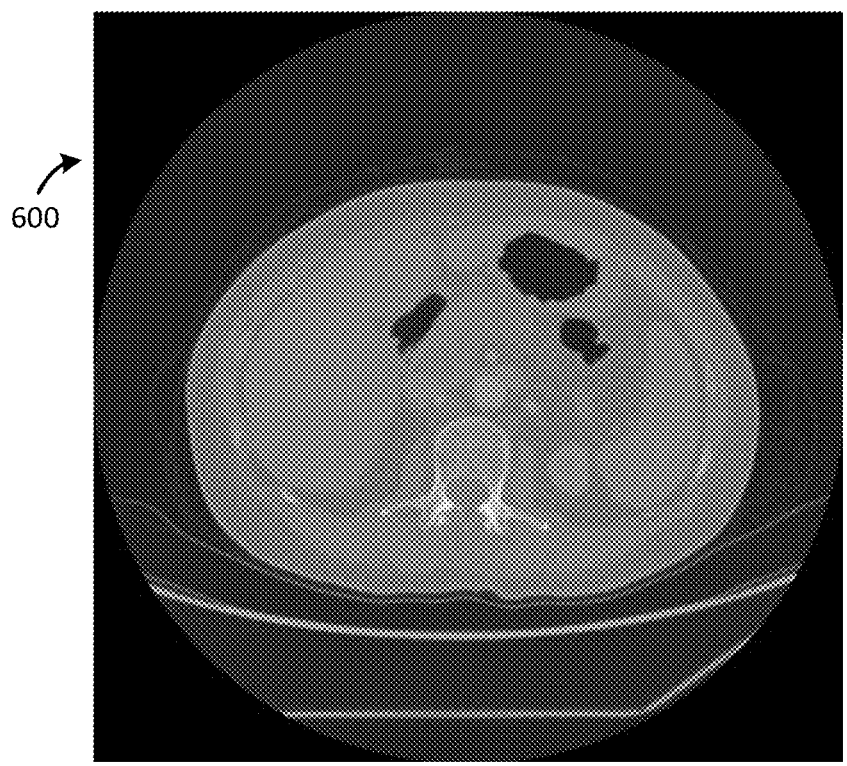
FIGS. 6A and 6B illustrate a ground truth CT image and a reconstructed monochromatic CT image, respectively, corresponding to the sinograms and x-ray intensities of FIGS. 5A through 5F.
Figure 6B:
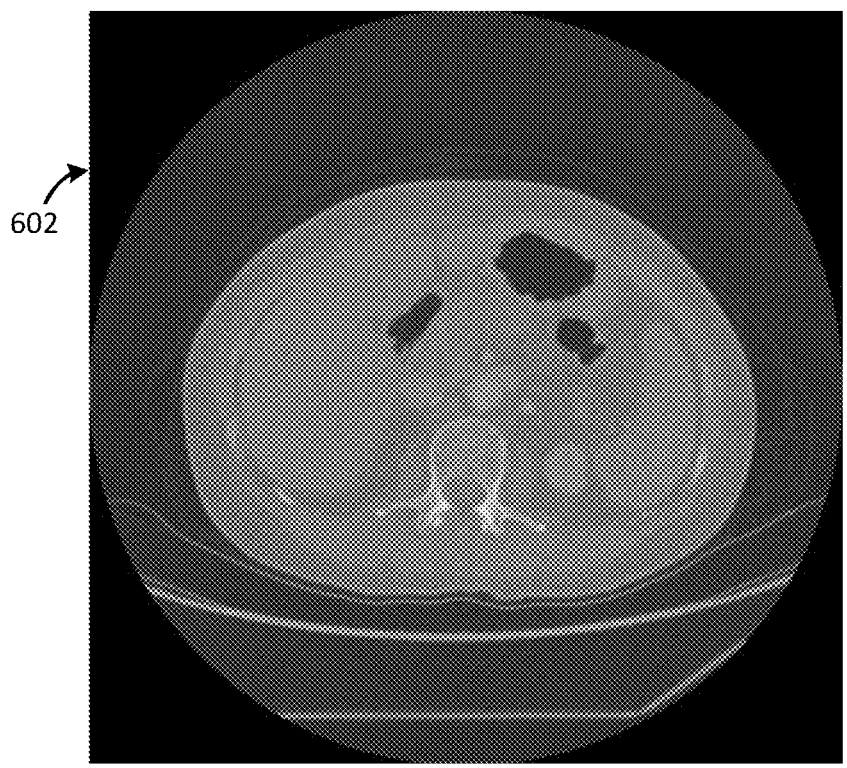

FIGS. 6A and 6B illustrate a ground truth CT image 600 and a reconstructed monochromatic CT image 602, respectively, corresponding to the sinograms and x-ray intensities of FIGS. 5A through 5F. It may be appreciated, by inspection, that the ground truth CT image 600 and reconstructed monochromatic CT image 602 are generally in agreement.

Qualitatively, in this example, the trained neural network delivered relatively high-quality monochromatic projection data in the testing phase, with a relative error less than 0.2%. CT image reconstruction was performed from monochromatic projection data using a simultaneous algebraic reconstruction technique (SART). Structural information was relatively well-preserved in the reconstructed monochromatic CT image including, for example, texture features, thus providing relatively superior image quality. The calculated peak-to-noise ratio (PSNR) and structural similarity (SSIM) for the reconstructed monochromatic image were 44.18 and 0.9698, respectively.

A method, apparatus and/or system consistent with the present disclosure is configured to target a fundamental level of the CT tomographic imaging workflow. The method, apparatus and/or system may be configured to implement deep learning with efficiency and effectiveness. For example, training operations for a plurality of views and/or a plurality of x-ray paths may be implemented, in parallel, on a graphics processing unit (GPU). To facilitate accuracy, uniqueness and stability of the solution, the training data set may be configured to include a relatively high quantity of images with well-diversified features.

Generally, a deep-learning-based image reconstruction technique may be utilized for monochromatic CT imaging when the x-ray source is polychromatic, and the x-ray detector is in the current-integrating mode. A nonlinear map (e.g., trained multilayer perceptron) may be determined between directly measured data and idealized line integrals through data-driven optimization. Due to big data based learning, the nonlinear mapping is configured to avoid the beam-hardening mechanism. Thus, the inverse Radon transform, such as filtered back projection (FBP), can be applied for monochromatic image reconstruction with relatively high accuracy. A system, method and/or apparatus, consistent with the present disclosure may be utilized for biomedical imaging, nondestructive testing, security screening, and/or other applications.

The energy-dependent non-linear integral equation on the basis of the Beer-Lambert law is an accurate physical model for x-ray CT, and is relatively complicated to be directly solved for the image reconstruction. The linear integral equation in the form of the Radon transform is an ideal computational model, and has an analytical inverse formula, such as filtered back projection (FBP), producing accurate and stable solution, while it is only an approximation to the non-linear integral equation, basically ignoring energy-dependent information, and generating inaccurate quantification of attenuation image and significant beam-hardening artifacts. The mismatch of computing model to physical model is also a fundamental problem in the x-ray computed tomographic imaging. The deep-learning-based sinogram correction method is configured to address the issue. The optimization of the neural network has a relatively good convergent performance in the big data learning process, and achieves a relatively high accuracy of the projection correction with a relative error of less than 0.2%, in some embodiments. This method learns a nonlinear transformation from big data to correct measured projection data to accurately match the linear integral model, realizing monochromatic imaging and overcome beam hardening effectively.

As used in any embodiment herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

"Circuitry", as used in any embodiment herein, may include, for example, singly or in any combination, hard-wired circuitry, programmable circuitry such as computer processors including one or more individual instruction processing cores, state machine circuitry, and/or firmware that stores instructions executed by programmable circuitry. The logic may, collectively or individually, be embodied as circuitry that forms part of a larger system, for example, an integrated circuit (IC), an application-specific integrated circuit (ASIC), a field-programmable gate array (FPGA), a programmable logic device (PLD), a complex programmable logic device (CPLD), a system on-chip (SoC), etc.

Memory 122 may include one or more of the following types of memory: semiconductor firmware memory, programmable memory, non-volatile memory, read only memory, electrically programmable memory, random access memory, flash memory, magnetic disk memory, and/or optical disk memory. Either additionally or alternatively memory 122 may include other and/or later-developed types of computer-readable memory.

Embodiments of the operations described herein may be implemented in a computer-readable storage device having stored thereon instructions that when executed by one or more processors perform the methods. The processor may include, for example, a processing unit and/or programmable circuitry. The storage device may include a machine readable storage device including any type of tangible, non-transitory storage device, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of storage devices suitable for storing electronic instructions.

What is claimed is:

1. A correction circuitry for computed tomography (CT) image reconstruction, the correction circuitry comprising:
    an artificial neural network (ANN); and
    a training circuitry configured to train the ANN based, at least in part, on training data, the training data comprising polychromatic CT image data as input data, and monochromatic projection data as output data.

2. The correction circuitry of claim 1, wherein the training data comprises one or more of a dual energy training data set, simulation data and/or experimental data.

3. The correction circuitry of claim 1, wherein the ANN is configured to map a CT image reconstructed from a single current-integrating data set to a monochromatic projection at a pre-specified energy level to realize monochromatic imaging.

4. The correction circuitry of claim 1, wherein the training data comprises a first number of training CT images having a second number of associated projection lines, the second number of associated projection lines greater than the first number of training CT images, each projection line comprising a plurality of pixels, and the ANN is trained using fewer than all of the pixels.

5. The correction circuitry of claim 1, wherein the CT image data is reconstructed from polychromatic projection data by a CT scanner.

6. A method for computed tomography (CT) image reconstruction, the method comprising:
    training, by a training circuitry, an artificial neural network (ANN) based, at least in part, on training data, the training data comprising polychromatic CT image data as input data, and monochromatic projection data as output data.

7. The method of claim 6, wherein the training data comprises one or more of a dual energy training data set, simulation data and/or experimental data.

8. The method of claim 6, further comprising mapping, by the ANN, a CT image reconstructed from a single current-integrating data set to a monochromatic projection at a pre-specified energy level to realize monochromatic imaging.

9. The method of claim 6, wherein the training data comprises a first number of training CT images having a second number of associated projection lines, the second number of associated projection lines greater than the first number of training CT images, each projection line comprising a plurality of pixels, and the ANN is trained using fewer than all of the pixels.

10. The method of claim 6, wherein the CT image data is reconstructed from polychromatic projection data by a CT scanner.

11. An apparatus for reconstructing a monochromatic computed tomography (CT) image, the apparatus comprising:
    a trained artificial neural network (ANN) configured to determine a monochromatic projection data set based, at least in part, on a measured CT image, the measured CT image reconstructed based, at least in part, on measured projection data, wherein the measured projection data is polychromatic; and
    reconstruction circuitry configured to reconstruct the monochromatic CT image based, at least in part, on the monochromatic projection data set.

12. The apparatus of claim 11, further comprising training circuitry configured to train the ANN based, at least in part, on one or more of a dual energy training data set, simulation data and/or experimental data.

13. The apparatus of claim 11, wherein the ANN is configured to map a CT image reconstructed from a single current-integrating data set to a monochromatic projection at a pre-specified energy level to realize monochromatic imaging.

14. The apparatus of claim 11, further comprising training circuitry configured to train the ANN based, at least in part, on a first number of training CT images having a second number of associated projection lines, wherein the second number of associated projection lines is greater than the first number of training CT images, each projection line comprises a plurality of pixels and the ANN is trained using fewer than all of the pixels.

15. The apparatus of claim 11, further comprising CT image reconstruction circuitry configured to reconstruct the measured CT image.

16. The apparatus of claim 11, wherein the ANN is a multilayer perceptron neural network.

17. The apparatus of claim 11, wherein the ANN comprises an input layer, an output layer and at least one hidden layer.

18. The apparatus of claim 11, wherein the measured CT image data is reconstructed from polychromatic projection data by a CT scanner.

19. The apparatus of claim 11, wherein the monochromatic CT image is reconstructed using a reconstruction technique selected from the group comprising filtered back projection (FBP), an iterative technique and/or a dictionary learning based technique.

20. The apparatus of claim 11, wherein the monochromatic projection data set is configured to reduce beam hardening artifacts in the monochromatic CT image compared to the measured CT image.

\* \* \* \* \*